US008679420B2

(12) United States Patent　　(10) Patent No.: US 8,679,420 B2
LaStella et al.　　(45) Date of Patent: *Mar. 25, 2014

(54) FECAL SAMPLING DEVICE AND METHOD

(75) Inventors: Vincent P. LaStella, Clark, NJ (US); Kenneth Kupits, Lanoka Harbor, NJ (US)

(73) Assignee: Immunostics, Inc., Ocean, NJ (US)

( * ) Notice: Subject to any disclaimer, the term of this patent is extended or adjusted under 35 U.S.C. 154(b) by 641 days.

This patent is subject to a terminal disclaimer.

(21) Appl. No.: 12/197,948

(22) Filed: Aug. 25, 2008

(65) Prior Publication Data

US 2010/0047129 A1　Feb. 25, 2010
US 2012/0003123 A9　Jan. 5, 2012

Related U.S. Application Data

(63) Continuation-in-part of application No. 10/896,607, filed on Jul. 22, 2004, now Pat. No. 7,427,505.

(51) Int. Cl.
*G01N 33/48* (2006.01)
(52) U.S. Cl.
USPC ........... 422/409; 422/401; 422/418; 422/420; 422/430; 436/66; 436/165
(58) Field of Classification Search
USPC ............ 422/401, 409, 418, 420, 430; 436/66, 436/165; 604/358
See application file for complete search history.

(56) References Cited

U.S. PATENT DOCUMENTS

| | | | |
|---|---|---|---|
| 2,291,173 A | 7/1942 | Simpson | 40/702 |
| 3,996,006 A | 12/1976 | Pagano | 23/253 |
| 4,092,120 A | 5/1978 | Suovaniemi et al. | |
| 4,112,165 A | 9/1978 | Russell | 428/134 |
| 4,225,557 A | 9/1980 | Hartl et al. | 422/56 |
| 4,259,964 A | 4/1981 | Levine | 600/371 |
| 4,273,741 A | 6/1981 | Levine | 422/56 |
| 4,333,734 A | 6/1982 | Fleisher | 436/66 |
| 4,365,970 A | 12/1982 | Lawrence et al. | 436/66 |
| 4,367,750 A | 1/1983 | Levine | 600/371 |
| 4,420,353 A | 12/1983 | Levine | 156/227 |
| 4,427,769 A | 1/1984 | Adlercreutz et al. | 435/7 |
| 4,486,536 A | 12/1984 | Baker et al. | 436/66 |
| D281,903 S | 12/1985 | Duffy | D24/225 |

(Continued)

FOREIGN PATENT DOCUMENTS

EP　　1619 502 A1　　1/2006
WO　　WO 90/03927　　4/1990

(Continued)

OTHER PUBLICATIONS

Extended European Search Report (Apr. 4, 2006).

(Continued)

*Primary Examiner* — Lyle Alexander
(74) *Attorney, Agent, or Firm* — Stroock & Stroock & Lavan LLP

(57) ABSTRACT

A device for testing a specimen comprising a first panel, a metering aperture structure having a plurality of metering apertures formed therein for receiving the specimen therethrough, a second panel opposite the first panel, a sheet disposed between the first and second panels, the sheet including a test area aligned with the plurality of metering apertures, a spacer element disposed between the first panel and the sheet, wherein the metering aperture structure is spaced away from the test area thereby improving readability of the testing. A method of manufacturing a specimen testing device is also disclosed.

14 Claims, 6 Drawing Sheets

(56) References Cited

U.S. PATENT DOCUMENTS

| | | | | |
|---|---|---|---|---|
| 4,559,949 A | 12/1985 | Levine | | 600/371 |
| 4,615,982 A | 10/1986 | Lawrence | | 436/66 |
| 4,645,743 A | 2/1987 | Baker et al. | | 436/66 |
| 4,789,629 A | 12/1988 | Baker et al. | | 422/61 |
| 4,804,518 A | 2/1989 | Levine et al. | | 422/56 |
| 4,808,379 A | 2/1989 | Wardlaw et al. | | 422/56 |
| 4,818,702 A | 4/1989 | Lawrence | | |
| 4,820,646 A | 4/1989 | Lawrence | | 436/66 |
| 4,937,197 A | 6/1990 | Lawrence | | 436/66 |
| 4,939,097 A | 7/1990 | Lawrence | | 427/96.9 |
| 4,942,132 A | 7/1990 | Lawrence | | 436/66 |
| 4,971,914 A | 11/1990 | Lawrence | | 436/66 |
| 5,053,342 A | 10/1991 | Lawrence | | 436/66 |
| 5,064,766 A | 11/1991 | Wardlaw et al. | | 436/66 |
| 5,068,197 A | 11/1991 | Lawrence | | 436/66 |
| 5,094,956 A | 3/1992 | Grow et al. | | 436/66 |
| 5,100,619 A | 3/1992 | Baker et al. | | 422/58 |
| 5,106,582 A | 4/1992 | Baker | | 422/58 |
| 5,150,971 A | 9/1992 | Strong et al. | | 383/84 |
| 5,171,529 A | 12/1992 | Schreiber | | 422/58 |
| 5,192,501 A | 3/1993 | Guadagno et al. | | 422/56 |
| 5,196,167 A | 3/1993 | Guadagno et al. | | 436/66 |
| 5,198,365 A | 3/1993 | Grow et al. | | 436/66 |
| 5,215,713 A | 6/1993 | Steinbiss et al. | | 422/61 |
| 5,217,874 A | 6/1993 | Guadagno et al. | | 435/28 |
| 5,264,181 A | 11/1993 | Schreiber | | 422/58 |
| 5,273,888 A | 12/1993 | Guadagno | | 436/66 |
| 5,310,680 A | 5/1994 | Baker et al. | | 436/66 |
| D351,475 S | 10/1994 | Gerber | | D24/223 |
| 5,391,498 A | 2/1995 | Baker et al. | | 436/66 |
| 5,411,893 A | 5/1995 | Eden et al. | | 422/58 |
| 5,447,868 A | 9/1995 | Augurt | | 436/66 |
| 5,563,071 A | 10/1996 | Augurt | | 436/66 |
| D383,215 S | 9/1997 | Levy | | D24/225 |
| 5,702,913 A | 12/1997 | Guadagno | | 435/28 |
| 5,747,344 A | 5/1998 | Cleator | | |
| 5,747,351 A | 5/1998 | Hemmati | | 436/514 |
| 5,939,252 A | 8/1999 | Lennon et al. | | |
| 5,948,687 A | 9/1999 | Cleator | | 436/66 |
| 6,006,911 A | 12/1999 | Levy | | 206/456 |
| D423,110 S | 4/2000 | Cipkowski | | D24/225 |
| D430,303 S | 8/2000 | Cipkowski | | D24/225 |
| 6,221,678 B1 | 4/2001 | Chandler | | 436/530 |
| 6,271,046 B1 | 8/2001 | Chandler | | 436/530 |
| 6,410,336 B1 | 6/2002 | Augurt | | 436/66 |
| 6,436,714 B1 | 8/2002 | Clawson et al. | | 436/66 |
| 7,189,356 B1 | 3/2007 | Clawson | | 422/56 |
| 7,288,413 B2 | 10/2007 | Goulden | | 436/66 |
| 2004/0053417 A1 | 3/2004 | Sinsky et al. | | 436/164 |
| 2006/0018789 A1 | 1/2006 | LaStella | | |
| 2008/0131971 A1 | 6/2008 | Clawson | | |

FOREIGN PATENT DOCUMENTS

| | | |
|---|---|---|
| WO | WO 90/13819 | 11/1990 |
| WO | WO 00/54029 | 9/2000 |
| WO | WO 02/080775 | 10/2002 |
| WO | WO 2009/152022 A1 | 12/2009 |

OTHER PUBLICATIONS

M. Beg,, et al; Occult Gastro-Intestinal Bleeding Detection, Interpretation, and Evaluation; Department of Medicine JN Medical College—Aligarh & Dr. RML Hospital-New Delhi; web publication on www.indigene.com/gas/featArt/indGasFeat10.html; pp. 1-6.

Allison, J., et al., A Comparison of Fecal Occult-Blood Tests for Colorectal-Cancer Screening; New England Journal of Medicine. 334:155-9, Jan. 18, 1996; web publication on www.journalclub.org.

Website: www.insuretest.com, undated.

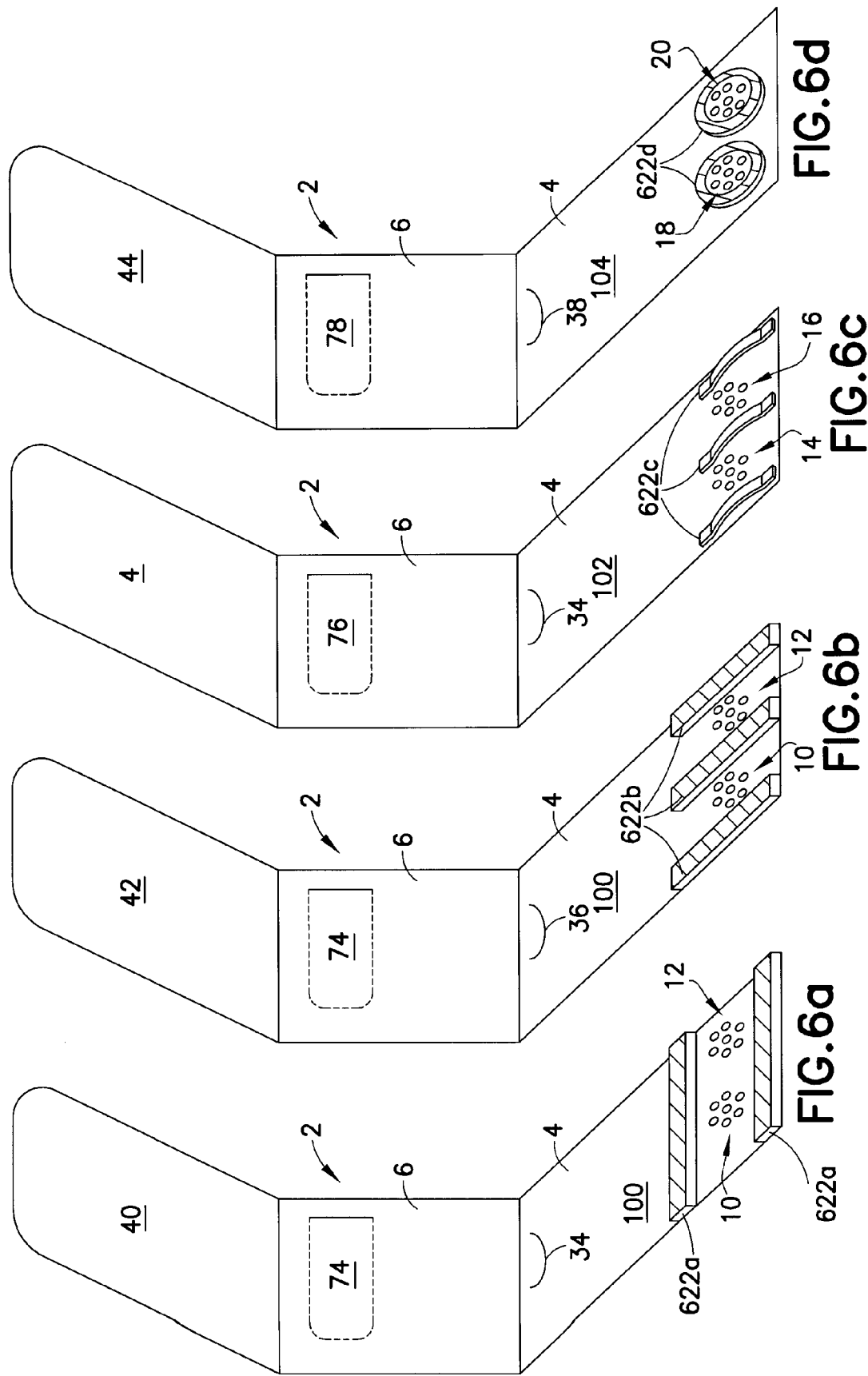

FECAL SAMPLING DEVICE AND METHOD

CROSS-REFERENCE TO RELATED APPLICATIONS

This application is a continuation-in-part under 35 U.S.C. §120 of U.S. patent application Ser. No. 10/896,607 filed Jul. 22, 2004, now U.S. Pat. No. 7,427,505, entitled FECAL OCCULT BLOOD TESTING DEVICE AND METHOD.

BACKGROUND OF THE INVENTION

1. Field of the Invention

The present invention relates, generally, to specimen collection and more particularly, to a method and device for collecting and determining the presence of occult blood in fecal matter and a test kit containing such a device.

2. Description of Related Art

Over 100,000 persons per year in the United States are afflicted with cancer of the colon and rectum. When the number of colon/rectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of about 80% to 90%. If, however, the disease is not detected until the later stages, the cure rate drops significantly. Thus, early detection of the disease is important to successful treatment of digestive tract cancer.

Most, but not all, cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Gross bleeding, however, is symptomatic of advanced cancers.

Digestive tract cancers in the early stages, including pre-cancerous polyps, also tend to bleed, giving rise to occult (hidden) blood in the fecal matter. Other pathological conditions, such as Crohn's disease and diverticulitis, can also give rise to the presence of occult blood in the fecal matter.

It is known that because of the relatively high fat content of fecal matter, blood, when present, is not distributed uniformly throughout it. For this reason, obtaining multiple samples from different areas of each bowel movement is desirable; but even a single positive test from any part of the feces should be considered a positive result.

Accordingly, test equipment and test procedures have been developed for use by physicians in testing for the presence of occult blood in fecal matter. There are two popular types of fecal sampling devices, wipe-style devices and slide-style devices.

An example of a wipe-type device is described in Levine U.S. Pat. No. 4,367,750 and an example of a slide-type device is described in U.S. Pat. No. 3,996,006. In general, whereas the wipe-type device includes a disposable layer that is wiped across the patient's anus to collect a sample and is then discarded, the slide-type device is not brought in contact with the patient's anus.

One drawback of existing devices is that the positive indication is often difficult to observe due to too much specimen being applied to the paper. Thus, a need exists for an improved fecal sampling device, including one having improved readability.

SUMMARY OF THE INVENTION

Embodiments of the present invention satisfy the foregoing, as well as other, needs. A device in accordance with one embodiment of the present invention has a specimen collection configuration, in which the specimen is collected, and a specimen testing configuration, in which the specimen is tested, the device comprising: a first panel; a metering aperture structure forming a plurality of metering apertures for receiving the specimen therethrough; a second panel opposite the first panel; a sheet including a test area, the sheet disposed between the first and second panels when the device is in the collection configuration and the test area aligned with the plurality of metering apertures, such that depositing the specimen through the plurality of metering apertures deposits the specimen on the test area when the device is in the collection configuration; a spacer element, which, when the device is in the testing configuration, is disposed between the first panel and the sheet, creating a space between the metering aperture structure and the test area.

In accordance with another embodiment of the present invention, there is provided a method of manufacturing a specimen testing device, the method comprising: forming a first panel, having a first end and a second end, and a second panel, where the first and second panel are coupled at the second end; overlaying the first panel on the second panel; forming a plurality of metering apertures in a metering aperture structure for receiving the specimen therethrough; interposing a sheet and a spacer element between the first panel and the second panel, the spacer element between the sheet and the first panel and proximate the metering apertures, the spacer element causing a space between the sheet and the metering aperture structure.

In yet another embodiment of the present invention there is provided a test kit including a specimen testing device described above; and one or more reagents for performing a test on specimens.

BRIEF DESCRIPTION OF THE DRAWINGS

Embodiments of the invention will now be described with reference to the accompanying drawings, in which:

FIGS. 6a-d are front views of alternate embodiments of the invention in an un-assembled state, without a sheet.

DETAILED DESCRIPTION OF EMBODIMENTS

Figure 1:
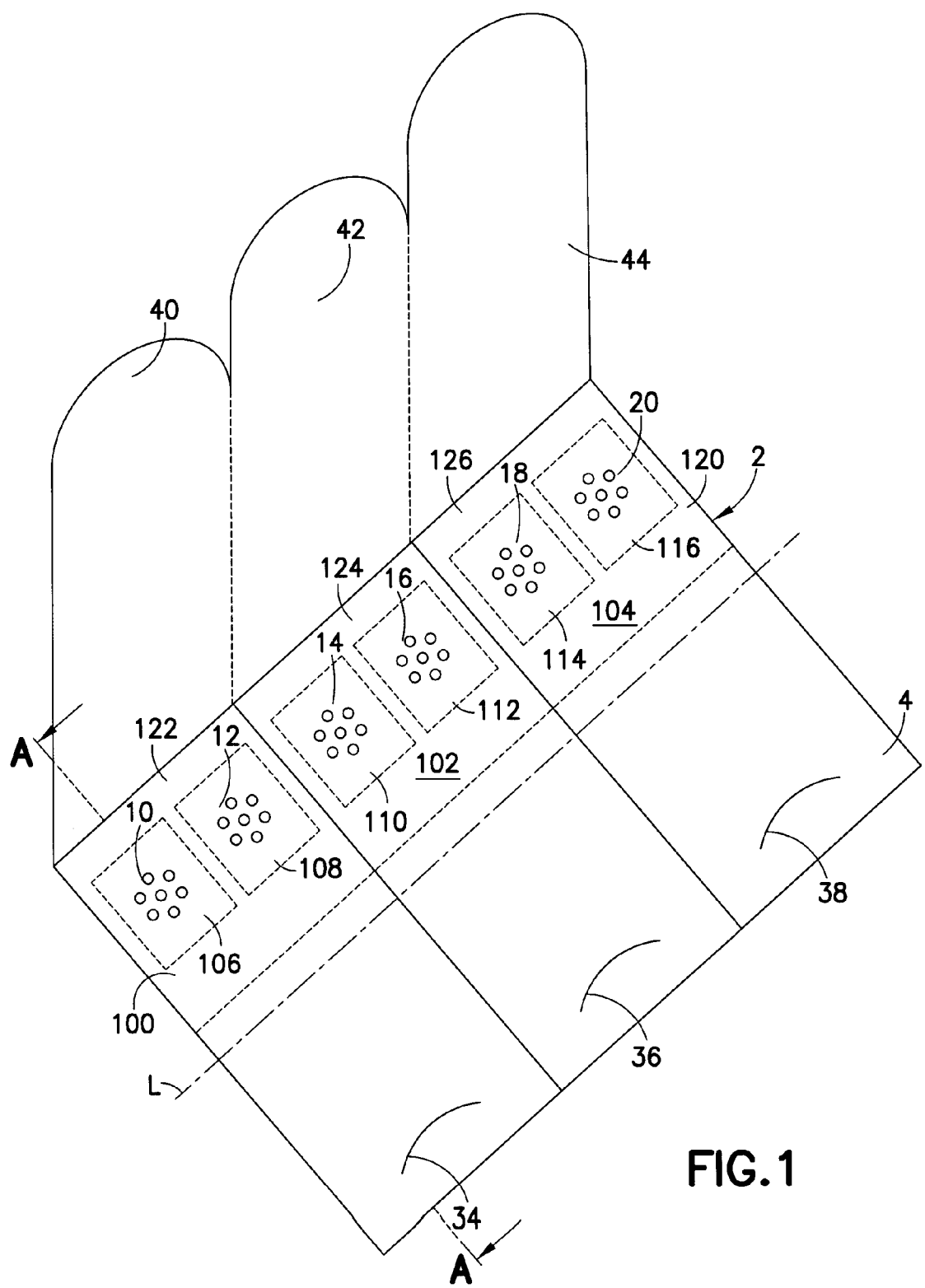
FIG. 1 is a front perspective view of a device according to one embodiment of the invention showing three testing areas with three covers in the open position.

Referring to FIGS. 1-5, a slide-type fecal occult blood testing device 2 according to one embodiment of the invention, is shown. The device 2 generally includes three test panels 100, 102, 104 (although any number may be provided on a separate device) and is formed of a first panel 4 and a second panel 6, with an absorbent sheet 8 disposed between the first and second panels 4, 6, on which a specimen is placed.

Each test panel 100, 102, 104 is configured to receive samples through apertures in the first panel 4 and into the test areas 8' of sheet 8. After receiving the specimen, the cover(s) 40, 42, 44 are closed, and the device 2 is turned over. Opening a flap 74, 76, 78 on one exterior of the device 2 (i.e., the second panel 6) exposes the test areas 8' of the sheet 8 on which the specimen was deposited. Developing solution is added via the apertures exposed by opening the flaps 74, 76, 78. In a typical guaiac test, a blue color denotes a positive test result.

More specifically, the first test panel 100 of panel 4 includes two groups of metering apertures 10, 12 in panel 4 for receiving samples. Similarly, the second test panel 102 includes two groups of apertures 14, 16 for receiving samples, and the third test panel 104 includes two groups of apertures 18,20 for receiving samples. The groups of apertures 10, 12, 14, 16, 18, and 20 are formed by the test panels 102, 104, 106. It should be understood that the arrangement of the apertures (which may be one or more groups of apertures) 10, 12, 14, 16, 18, for receiving samples can include, but are not limited to, an oval, circle, square, rectangle, linear series, and other shapes and arrangements, and each individual aperture may be any size or shape such as, for example square, rectangle, triangle, or circle. In further embodiments, the plurality of metering apertures can be a mesh, a permeable membrane, a woven material or other material. Furthermore, although the metering apertures of the present embodiment are formed directly in the first panel 4, it should be understood that the metering apertures of other embodiments can be formed by one or more tabs, strips, or other structures overlaying an aperture or apertures in the first panel.

Figure 5:
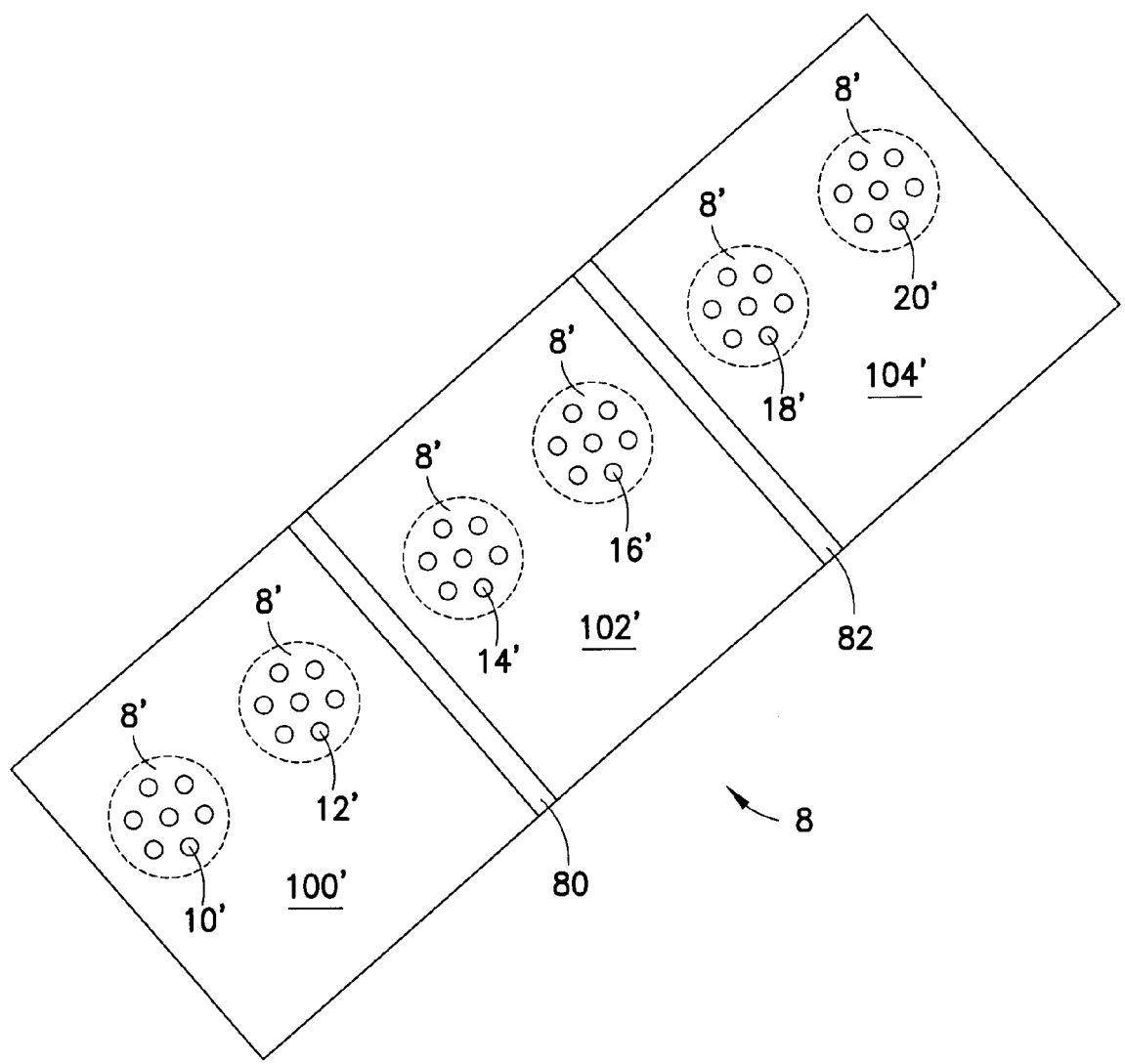
FIG. 5 is a front view of a sheet according of the device of FIGS. 1-4.

It should also be appreciated that, as compared to a single, large aperture, as shown in FIG. 5, each plurality of smaller apertures 10, 12, 14, 16, 18, 20 preferably meters or controls the amount and configuration of the sample 10', 12', 14', 16', 18', or 20' that gets deposited on the test areas 8' of sheet 8 by receiving a portion of the sample and obscuring a portion of the sheet 8, thereby creating multiple spaced samples. Rather than a relatively large, thick sample, which can obscure the reading of the test results, the relatively smaller, spaced samples permit easier reading, as the developing solution, and thus the color, is able to permeate the space on sheet 8 between samples. The present inventors have discovered, however, that the readability of even the metered sample can be improved. It has been found that the structure forming the metering apertures 10, 12, 14, 16, 18, and 20 can restrict or retard the developing solution, and thus the color test indicator, from permeating through the sheet 8 when the area of test panels 100, 102, 104 forming metering holes 10, 12, 14, 16, 18, and 20 is in contact (including partial contact) with the sheet 8. Accordingly, the present embodiment includes a spacer element 120, as further discussed below.

Figure 2:
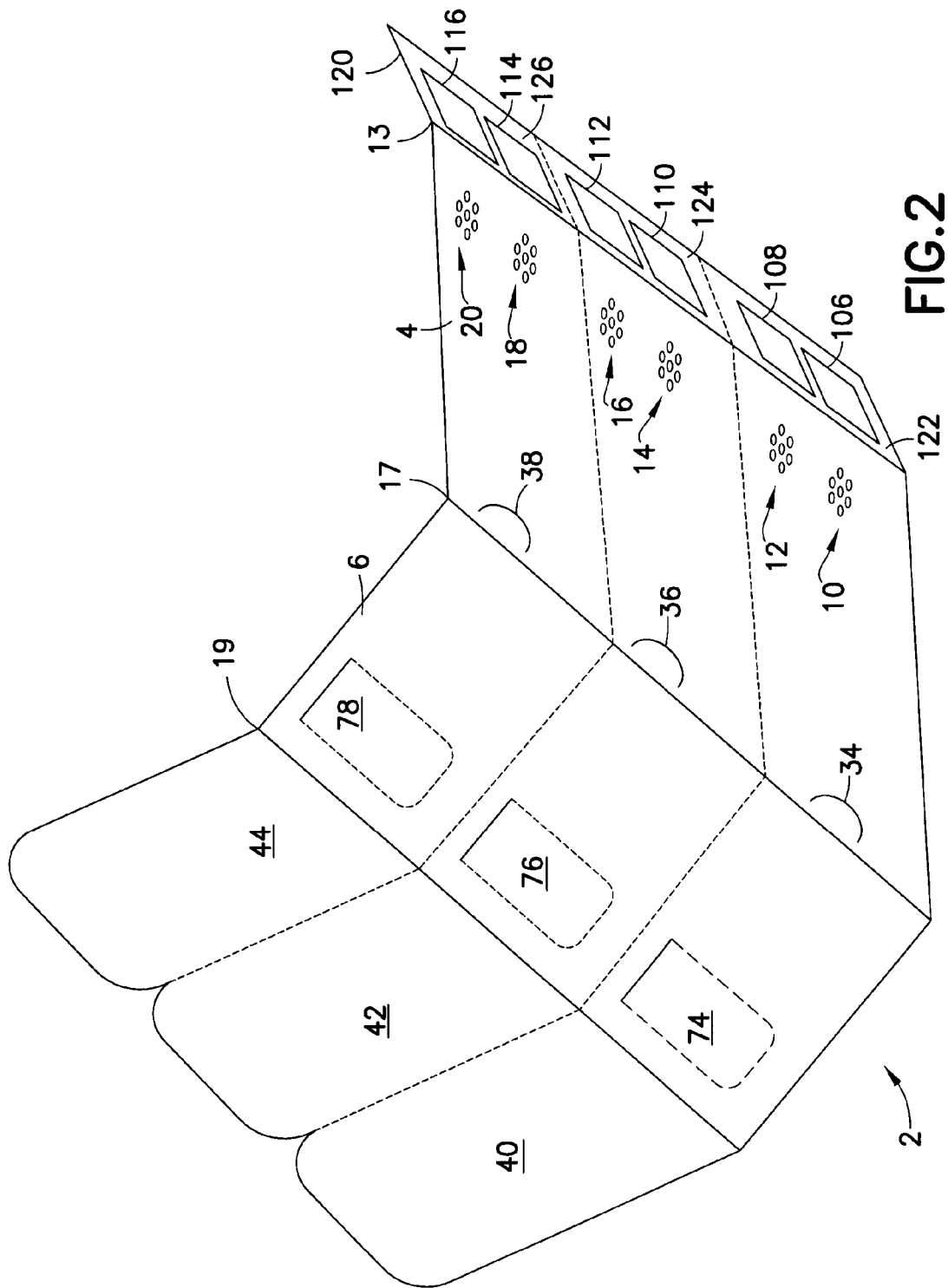
FIG. 2 is a perspective view of the device of FIGS. 1, 3, and 4 in an un-assembled state, without the sheet.
Figure 3:
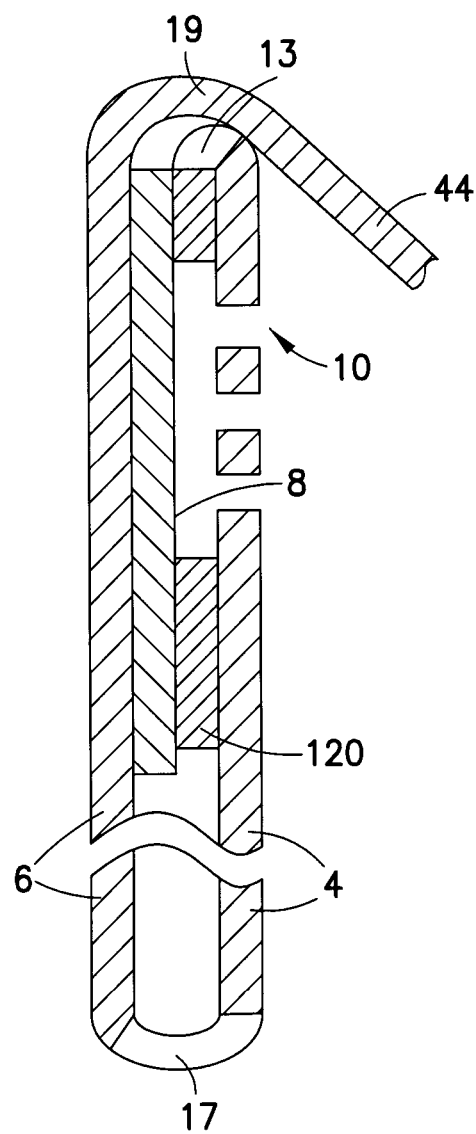
FIG. 3 is a cross sectional view of the device of FIGS. 1 and 2 taken along axis A-A.

To increase readability during testing, each test panel 100, 102, 104 is provided with a spacer element 122, 124, 126 (generally, 120). The spacer element 120 can be integral with the front panel 4 (as shown in FIG. 2), or it may be a separate, additional panel or one or more additional pieces (e.g., in the interior of the device, such as adhered to the inner surface of the first panel 4, as shown in FIGS. 6a-d). Each spacer element 122, 124, 126 is generally positioned behind or adjacent the metering apertures 10, 12, 14, 16, 18, 20 and includes one or more apertures 106, 108, 110, 112, 114, and 116 that are aligned with a corresponding group of metering apertures 10, 12, 14, 16, 18, and 20 such that the samples passing through the metering apertures 10, 12, 14, 16, 18 and 20 also pass through the apertures 106, 108, 110, 112, 114, and 116 of the spacer elements 122, 124, 126 and are deposited on the test areas 8' of sheet 8. As illustrated in FIG. 2, each spacer element 122, 124, 126 preferably has a depth or thickness that creates a distance or space between the sheet 8 and at least a portion of the structure (in this embodiment, the first panel 4) forming the metering apertures 10, 12, 14, 16, 18, and 20. For example, a thickness in the range of 10-12 pt (or mils) is sufficient when the device 2, including the spacer element 120, is made of coated paper board, such as that provided by Avery Dennison Corporation under the tradenames FASSON RAPID-ROLL C1S GALERIE®, FASSON C1S CAROLINA® and FASSON C2S CAROLINA®. However, spacer element 120 (and/or the device 2) may also be made from other materials having greater and smaller thicknesses, manufactured by other entities.

It should also be noted that the spacer element apertures 106, 108, 110, 112, 114, 116 may be any shape or configuration so long as the sample deposited through metering apertures 10, 12, 14, 16, 18, 20 can pass through the spacer element apertures 106, 108, 110, 112, 114, 116 and get deposited onto test area 8' of sheet 8.

Although the spacer elements 122, 124, 126 of the present embodiment are shown as including apertures, in certain alternate embodiments, the spacer element may be a plurality of discrete strips of paper or other material on some, or all, sides of the test areas 8 (such as spacer elements 622a-c in FIGS. 6a-c), a ring adhered to sheet 8 or panel 4 (such as spacer element 622d in FIG. 6d), or any other element capable of spacing at least a portion of sheet 8 from other structures creating or surrounding the metering apertures.

Returning to FIGS. 1-5, each of the three test panels 100, 102, 104 also has a cover 40, 42, 44, respectively. Each cover 40, 42 and 44 is engageable with a corresponding flap formed by arcuate slit 34, 36, 38, respectively, which is used to maintain the covers in a closed position, after the samples are obtained.

Figure 4:
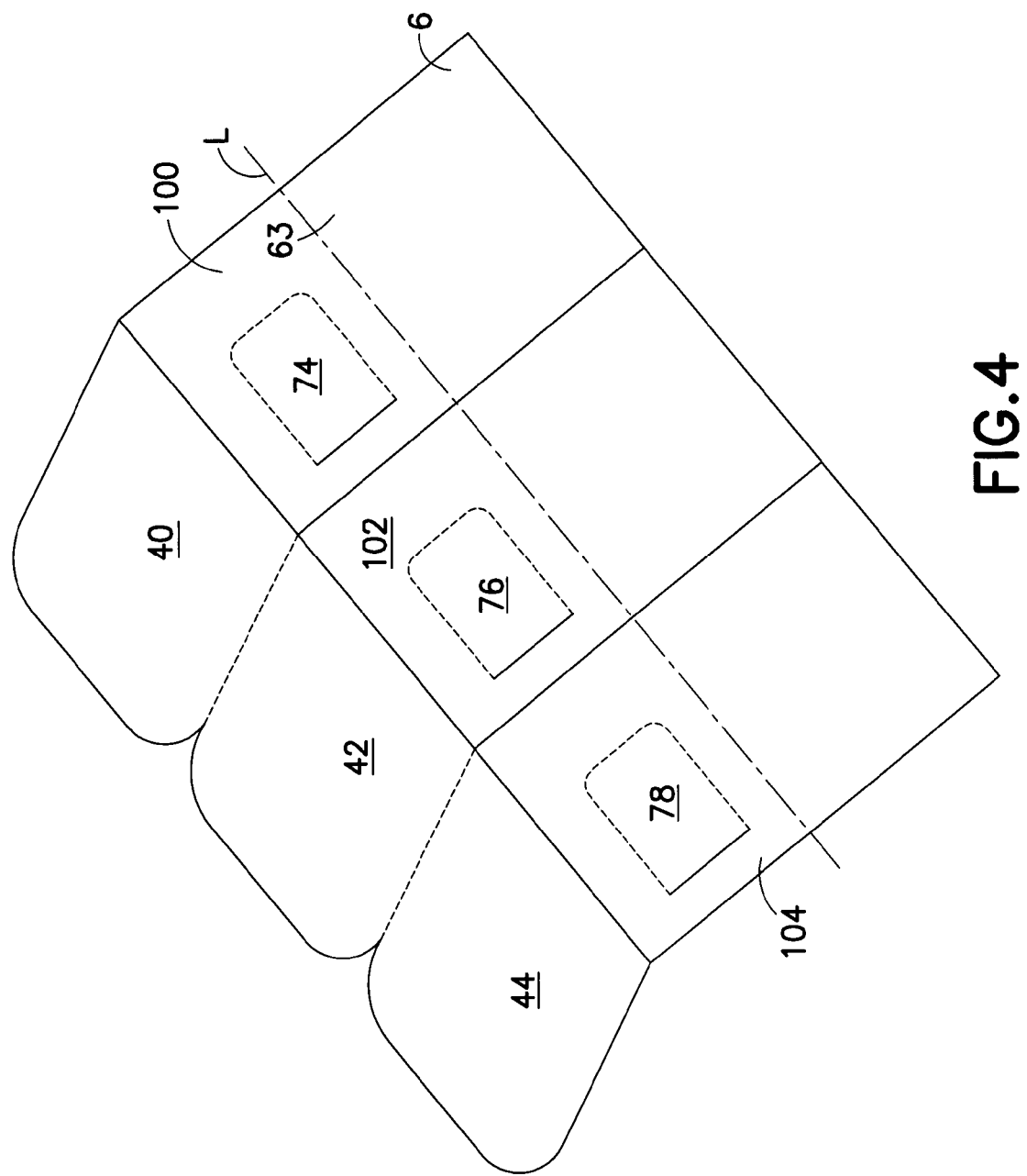
FIG. 4 is a rear perspective view of the device of FIGS. 1-3.

As shown in FIGS. 2 and 4, each test panel 100, 102, 104 includes a flap 74, 76, 78 which is aligned with the metering apertures 10, 12, 14, 16, 18, 20 of the first panel 4 and thus, the test areas 8' of sheet 8. For example, test panel 100 includes a flap 74 aligned with the plurality of metering apertures 10 and 12 in such a way that opening of flap 74 exposes the test areas 8' of sheet 8, which is aligned with the plurality of metering apertures 10 and 12. As discussed below, the flaps 74, 76, 78 are opened to allow a developing solution to be placed on the test areas 8' of sheet 8 when performing a test.

In the present embodiment, as illustrated in FIG. 5, the sheet 8 is a single piece of filter paper generally dimensioned to cover, and align with, at least the test apertures 10, 12, 14, 16, 18, 20 such that depositing a sample through the apertures 10, 12, 14, 16, 18, 20 deposits the sample onto the test areas 8' of sheet 8. In alternative embodiments, however, the sheet is dimensioned to cover the entire panel 6.

In certain embodiments, sheet 8 is made of an absorbent material, and is typically filter paper impregnated with a reagent which will react with hemoglobin components from blood and a developing solution (e.g., peroxide) to form a colored compound. Examples of suitable reagents are guaiac, tetraethyl benzidene, orthotoluidine and other similar chromogens, but any type of test may be used. In the embodiment illustrated herein, the reagent impregnated in sheet 8 is guaiac. Here, at least the test areas 8' corresponding to the plurality of metering apertures 10, 12, 14, 16, 18 and 20 are impregnated with the reagent.

To reduce risk of cross-contamination, prevent or minimize possible leakage of developing solution and to ease separation of the three sheet panels 100', 102', 104', the test panels 100, 102, 104 are separated from each other by dividing regions 80 and 82, all of which may comprise a hydrophobic material, for example wax, glue or other suitable material. Alternatively, the test area 8' may be comprised of separate pieces of filter paper separated by a hydrophobic barrier. In still another embodiment, the samples are separated by a crimp or other physical barrier, for example, comprised of one or more of the panels 4, 6 themselves. As will be understood, the degree to which the sheet panels 100', 102', 104' and the test areas 8' are separated is dependent upon the tendency of the material used to manufacture the device to be affected by contamination. Furthermore, the device may comprise a single sheet.

As illustrated in FIG. 2, the panels 4, 6, covers 40, 42, 44, and spacer element 120 can be (but need not be) formed of a single sheet of paper, cardboard or other suitable material, in which the apertures, slits, tabs and perforations are die-cut. The device 2 is assembled by overlaying spacer element 120 (e.g., with the spacer element 120 and panel 4 coupled along an end 13), on the inner surface of panel 4, and overlaying panel 4 on panel 6 (e.g., with the first 4 and second 5 panels coupled along a second end 17), with the sheet 8 therebetween, and overlaying the cover 40, 42, 44 over panel 4 (e.g., with the covers 40, 42, 46 and second panel 6 coupled along a third end 19). The assembly can be held together by the structural stability of the material used in making the panels, or by the use of a suitable glue, adhesive, or through use of coupling structures such as, for example, crimps, folds, staples, or clips. Although not required, to minimize sticking of the covers to the specimen, the panels 4 and 6 are provided on their inner surfaces with a layer of non-stick material, typically a wax layer, although other materials may be used.

The covers 40, 42 and 44 (where provided) for first panel 4 may be provided with appropriate printed matter to assist the patient, physician and/or laboratory. For example, the patient's name, address and instructions on how to use the device may be printed on the covers 40, 42 and 44. Such instructions may include instructing the patient to apply a specimen from the same areas of the fecal matter, or even the same smear onto sample apertures 10, 12, 14, 16, 18, 20. Other printed matter that may also be provided on the first panel 4 includes for example, the sample number and the test to be performed. Printed matter may also be provided on the second panel 6. For example, instructions to the doctor as to how to carry out testing by opening any flaps and/or tabs on second panel may be provided.

In an alternate embodiment, the device is manufactured with the spacer element coupled to the second panel and the covers coupled to the first panel. In such an embodiment, the device may be formed from a single sheet of paper or other stratum, with the second panel connected to the first panel (e.g., along a fold) at one end of the second panel, and the second panel connected to the spacer element at the opposite end of the second panel (e.g., along another fold), the spacer element being folded inwards, between the first and second panels. The cover is connected to the end of the first panel opposite the end connected to the second panel, the cover being folded forward to overlay the outer surface of the first panel.

In a further embodiment, panel 4 can be provided with indicating means for locating where specimen is to be placed on the sheet. The indicating means may comprise printed circles or other shapes on the panel as a visible indicator to the user of where to place the specimen.

With regard to the embodiment of FIGS. 1-5, where a fecal sample is to be analyzed, the device 2 is typically sent home with a patient. The patient opens the cover 40 on the first panel 4 of the device and, while the device is in the specimen collection configuration, smears a first fecal specimen through metering apertures 10 on test panel 100, thereby depositing samples on the exposed test area 8' of sheet 8. A second fecal specimen, for example, taken at a different time as a result of a different bowel movement or from a different region of the same bowel movement as the first specimen, is then smeared through other corresponding metering apertures 12 of test panel 100, onto the exposed test area 8' of sheet 8. This may be performed any number of times, using any one or more test panels 100, 102, 104. Then the patient preferably closes the covers 40, 42, 44 and secures them in the arcuate slits 34, 36, 38.

The patient obtains the requisite number of samples and typically either returns the device to the physician or to a laboratory.

To conduct the test or analysis on the specimens, the flap 74 on second panel 6 overlaying the apertures 10, 12 of the first test panel 100, through which the specimens have been applied, is opened and while the device is in the testing configuration, developing solution is applied to the exposed rear surface of sheet 8. The space between sheet 8 and panel 4, provided by the spacer element 120, improves the readability and ability to interpret the test result after applying the developing solution.

According to an additional embodiment, the testing device may be provided individually or may be packaged in kit form. For example, kits might be prepared comprising numerous testing devices, reagents required to perform the primary analysis for such devices, such as the developing solution used in the guaiac test.

Embodiments of the present invention enjoy numerous advantages. For example, the device can be embodied in one card that readily facilitates transference between the doctor and the patient and between the doctor and another testing location, such as a laboratory. The device is easy to use by the patient, provides an easy to read test result and is inexpensive to produce.

Those skilled in the art will recognize that the method and system of the present invention has many applications, may be implemented in many manners and, as such, is not to be limited by the foregoing exemplary embodiments and examples. In this regard, any number of the features of the different embodiments described herein may be combined into one single embodiment, and all features of a given embodiment need not be included in other embodiments. Moreover, the scope of the present invention covers conventionally known and future developed variations and modifications to the components and materials described herein, as would be understood by those skilled in the art.

Furthermore, although certain embodiments are shown with three test panels for testing three bowel movements, with multiple samples or specimens from each, other numbers of panels and/or samples/specimens may be provided and taken.

The embodiments of the invention has been described with reference to analysis of fecal samples for stool occult blood. However, the device may be used for screening and testing of other biological specimens, for example blood and AIDS tests, urine tests and pregnancy tests.

While the present invention has been described in considerable detail, the invention disclosed herein is not limited to the detailed description, and is to be afforded the full scope of the appended claims and all equivalents thereto.

What is claimed is:

1. A device having a specimen collection configuration, in which one or more specimens are collected, and a specimen testing configuration, in which the one or more specimens are tested, the device comprising:
   a first panel;
   one or more metering aperture structures disposed on the first panel, each metering aperture structure comprising one or more groups of metering apertures, each group of metering apertures for receiving a separate one of the one or more specimens therethrough;

a second panel opposite the first panel;

a sheet including one or more test areas, the sheet disposed between the one or more metering aperture structures and second panel when the device is in the collection configuration and each test area aligned with a separate one of the groups of metering apertures, such that depositing the specimen through one of the groups of metering apertures deposits the specimen on the test area aligned therewith when the device is in the collection configuration;

a spacer element, which, when the device is in the testing configuration, is disposed between the metering aperture structure and the sheet, creating a space between the metering aperture structure and the test area.

2. The device of claim 1, wherein the spacer element is a third panel.

3. The device of claim 2, wherein the spacer element includes at least one aperture aligned with one of the groups of metering apertures when the device is in the testing configuration.

4. The device of claim 1, wherein the spacer element is integral with the first panel.

5. The device of claim 1, wherein the spacer element is integral with the second panel.

6. The device of claim 1, wherein the first panel, the second panel, and the spacer element are formed from a single piece of material and are hingably connected to each other along a fold.

7. The device of claim 1, wherein the second panel includes a flap, the flap covering an aperture in the second panel that is aligned with one of the one or more test areas.

8. The device of claim 1, wherein the spacer element is at least one strip of material adjacent one of the groups of metering apertures.

9. The device of claim 1 wherein at least one of the one or more metering aperture structures is integrally formed in the first panel.

10. The device of claim 1 wherein at least one of the one or more metering aperture structures is separately formed and is disposed on the first panel.

11. The device of claim 1 wherein, in the specimen testing configuration, the one or more test areas are free of contact with any other structure of the device.

12. The device of claim 1 wherein the space is between at least a portion of one of the one or more metering aperture structures and at least a portion of the test area aligned with the one metering aperture structure.

13. The device of claim 1 wherein the space is between one of the one or more metering aperture structures and the entire test area aligned with the one metering aperture structure.

14. The device of claim 1 including two or more groups of metering apertures and two or more test areas.

* * * * *